(12) United States Patent
Becker et al.

(10) Patent No.: US 8,173,803 B2
(45) Date of Patent: May 8, 2012

(54) SUPRAMOLECULAR SCAFFOLDS AND METHODS OF MAKING THE SAME

(75) Inventors: Daniel P. Becker, Glenview, IL (US); Andria M. Panagopoulos, Chicago, IL (US); Marlon R. Lutz, Jr., Chicago, IL (US)

(73) Assignee: Loyola University of Chicago, Chicago, IL (US)

( * ) Notice: Subject to any disclaimer, the term of this patent is extended or adjusted under 35 U.S.C. 154(b) by 386 days.

(21) Appl. No.: 12/541,352

(22) Filed: Aug. 14, 2009

(65) Prior Publication Data
US 2010/0041880 A1    Feb. 18, 2010

Related U.S. Application Data

(60) Provisional application No. 61/089,087, filed on Aug. 15, 2008.

(51) Int. Cl.
C07D 487/00    (2006.01)
(52) U.S. Cl. ........................................ 540/471
(58) Field of Classification Search ........................ None
See application file for complete search history.

(56) References Cited

PUBLICATIONS

Panagopolous. Abstracts of Papers, 236th ACS National Meeting, 2008.*
Acosta et al., Oxidative demethylation of 4-substituted N,N-dimethylanilines with iodine and calcium oxide in the presence of methanol, *J.Chem. Soc. Chemical Communications*, 1985-1986 (1994).
Ahmad et al., Building cyclotriveratrylene host molecules into network structures. *Cryst Eng Comm* 4: 227-231 (2002).
Ahmad et al., Hydrogen-bonded superstructures of a small host molecule and lanthanide aquo ions, *Inorg. Chem.*, 42:2182-2184 (2003).
Ahmad et al., Synthesis and structural studies of cyclotriveratrylene derivatives. *Supramolecular Chemistry*, 18: 29-38 (2006).
Atkins, Tricyclic trisaminomethanes, *J. Am. Chem. Soc.*, 102:6364-6365 (1980).
Baran et al., Total synthesis of (+-)-haouamine A, *J. Am. Chem. Soc.*, 128:3908-3909 (2006).
Battle et al., Molecular structure and hydrolytic stability amidinium salts derived from triazatricyclo[5.2.1.04,10]decane, *Tetrahedron*, 61:7499-7507 (2005).
Beer et al., Anion sensing by metal-based receptors, *Top. Curr. Chem.*, 255:125-162 (2005).
Benniston et al., The synthesis of small azamacrocycles bearing pendant aromatic functionalities. The crystal structures of [Cu(L1)2](PF6)2, [(L1)CuCl2], [Cu(L6)(NO3)2] and [Cu2(L7-H)2(OH2)2](PF6)2.3H2O (L1=N-(mesitylethyl)-1,4,7-triazacyclononane, L6=N-(4-hydroxymethylbenzyl)-1,4,7-triazacyclononane, L7=N-(4-benzylcarboxylic acid)-1,4,7-triazacyclononane), *Polyhedron*, 21: 333-342 (2002).
Black et al., Metal template reactions. XVI. Design and synthesis of primary diamine ligands with additional nitrogen donor atoms, *Aust. J. Chem.*, 36:1141-1147 (1983).
Bowman-James, Book Review: Anion Sensing. Topics in Current Chemistry, *J. Am. Chem. Soc.* 128:2502 (2006).
Burlinson et al., Characterization of cyclotriveratrylene inclusion compounds by means of solid state carbon-13 NMR, *J. Inclusion Phenomena*, 1:403-409 (1984).
Caira et al., Inclusion compounds of cyclotriveratrylene (2,3,7,8,12,13-hexamethoxy-5,10-dihydro-15H-tribenzo[a,d,g]cyclononene) with chlorinated guests, *Supramolecular Chemistry*, 16:337-342 (2004).
Cameron et al., Anionic cyclophanes as potential reversal agents of muscle relaxants by chemical chelation, *Bioorg. Med. Chem. Lett.*, 12:753-755 (2002).
Campos et al., Synthesis, molecular modeling, and pharmacological testing of bis-quinolinium cyclophanes: potent, non-peptidic blockers of the apamin-sensitive $Ca^{2+}$-activated $K^+$ channel, *J. Med. Chem.*, 43:420-431 (2000).
Chamorro et al., Approaches to the solid phase of a cyclotriveratrylene scaffold-based tripodal library as potential artificial receptors, *J. Comb. Chem.*, 5:794-801 (2003).
Chen et al., Bis-quinolinium cyclophanes: 8,14-Diaza-1,7(1,4)-diquinolinacyclotetradecaphane (UCL 1848), a highly potent and selective, nonpeptidic blocker of the apamin-sensitive $Ca^{2+}$-activated $K^+$ channel, *J. Med. Chem.*, 43:3478-3481 (2000).
Chistyakov et al., Crown compounds for anions. A new approach to the description of chemical bonds in the complexes of halide anions with polymercury-containing macrocycles, *J. Organometallic Chem.*, 536/537:413-424 (1997).
Cho et al., Synthesis and characterization of 4'-amino and 4'-nitro derivatives of 4-N,N-dimethylaminotriphenylmethane as precursors for a proximate malachite green metabolite, *Tetrahedron*, 56:7379-7388 (2000).
Chong et al., Synthesis and evaluation of novel macrocyclic and acyclic ligands as contrast enhancement agents for magnetic resonance imaging, *J. Med. Chem.*, 49:2055-2062 (2006).

(Continued)

Primary Examiner — Noble Jarrell
(74) Attorney, Agent, or Firm — Marshall, Gerstein & Borun LLP

(57) ABSTRACT

Tribenzo-1,4,7-triazacyclononane and derivatives thereof having a formula (I) are disclosed. Methods of making tribenzo-1,4,7-triazacyclononane and related compounds also are disclosed.

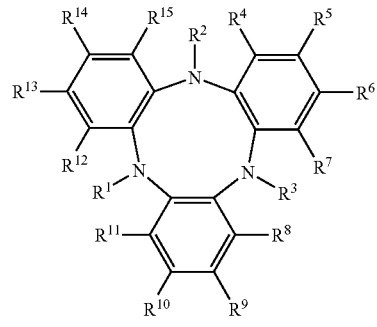

14 Claims, No Drawings

PUBLICATIONS

Christian et al., Comparison of the capacity of beta-cyclodextrin derivatives and cyclophanes to shuttle cholesterol between cells and serum lipoproteins, *J. Lipid Res.*, 40:1475-1482 (1999).

Collet et al., Cyclotriveratrylenes and cryptophanes: their synthesis and applications to host-guest chemistry and to design of new materials, *Top. Curr. Chem.*, 165:103-129 (1993).

Conejo-Garcia et al., Bispyridinium cyclophanes: novel templates for human choline kinase inhibitors, *J. Med. Chem.*, 46: 3754-3757 (2003).

Cope et al., Tertiary amines from methiodides and lithium aluminum hydride, *J. Am. Chem. Soc.*, 82:4651-4655 (1960).

Cortright et al., Hydrogen from catalytic reforming of biomass-derived hydrocarbons in liquid water. *Nature*, 418: 964-967 (2002).

Davis et al., The construction and operation of anion sensors: current status and future perspectives, *Top. Curr. Chem.*,255:97-124 (2005).

Dudic et al., Calix[4]arene-porphyrin conjugates as versatile molecular receptors for anions, *Org. Lett.*, 5:149-152 (2003).

Dussalt et al., Studies of copper(II) and nickel(II) complexation by bis(1,4,7-triazacyclononane) ligands containing alkene and alkyne bridging groups, *Inorg. Chim. Acta*, 357:1478-1486 (2004).

Ettmayer et al., Paracyclophanes: a novel class of water-soluble inhibitors of HIV proteinase, *J. Med. Chem.*, 39: 3291-3299 (1996).

Fukushima et al., Azacalix[n]arenes with-NH-amino group: NH . . . OCH3 interaction-assisted synthesis, structure, and reactivity. *Synlett*, 19:2931-2934 (2005).

Galanakis et al., Bis-quinolinium cyclophanes: toward a pharmacophore model for the blockade of apamin-sensitive SKCa channels in sympathetic neurons,*Bioorg. Med. Chem. Lett.*, 14:4231-4235 (2004).

Garrido et al., Haouamines A and B: A new class of alkaloids from the ascidian Aplidium haouarianum, *J. Org. Chem.*, 68:293-299 (2003).

Gorvin, The synthesis of di- and triarylamines through halogen displacement by base-activated arylamines: comparison with the Ullmann condensation, *J. Chem. Soc., Perkin Transactions 1: Organic and Bio-Organic Chemistry* (1972-1999), 1331-1335 (1988).

Gronert et al., Identity hydride-ion transfer from C—H donors to C acceptor sites. Enthalpies of hydride addition and enthalpies of activation. comparison with C . . . H . . . C proton transfer. An ab initio study, *J. Am. Chem. Soc.*, 127:2324-2333 (2005).

Hartwig, Approaches to catalyst discovery. New carbon-heteroatom and carbon—carbon bond formation, *Pure and Applied Chemistry*, 71:1417-1423 (1999).

Hartwig, Carbon-heteroatom bond-forming reductive eliminations of amines, ethers, and sulfides, *Acc. Chem. Res.*, 31: 852-860 (1998).

Hey et al., Intranuclear cyclisation. Part V. The cyclisation of derivatives of diphenylmethane, benzophenone, and N-methyldiphenylamine, *J. Chem. Soc.*, 2276-87 (1952).

Holman et al., Deep cavity [CpFe(arene)]$^+$ derivatized cyclotriveratrylenes as anion hosts, *Chem. Commun. (Cambridge)*, 2109-2110 (1998).

Hone et al., Rapid, quantitative colorimetric detection of a lectin using mannose-stabilized gold nanoparticles, *Langmuir*, 19:7141-7144 (2003).

Huber et al., NMR study of optically active monosubstituted cryptophanes and their interaction with xenon. *J. Phys. Chem. A*, 108:9608-9615 (2004).

Iranzo et al., Cooperativity between metal ions in the cleavage of phosphate diesters and RNA by dinuclear Zn(II) catalysts, *Inorg. Chem.*, 42:7737-7746 (2003).

Ito et al., N-methyl-substituted Aza[1n]metacyclophane: preparation, structure, and properties. *J. Org. Chem.* 64:8236-41 (1999).

Kolusheva et al., Color fingerprinting of proteins by calixarenes embedded in lipid/polydiacetylene vesicles, *J. Am. Chem. Soc.*, 128:13592-13598 (2006).

Konarev et al.,The formation of a single-bonded $(C70^-)_2$ dimer in a new ionic multicomponent complex of cyclotriveratrylene: $(CS^+)_2(C_{70}^-)_2$·CTV·$(DMF)_7(C_6H_6)$0.75, *Chem. Commun. (Cambridge)*, 2548-2549 (2002).

Liang et al., Amido pincer complexes of nickel(II): Synthesis, structure, and reactivity, *Organometallics*, 25:1399-1411 (2006).

McGowan et al., N-Monofunctionalized 1,4,7-triazacyclononane macrocycles as building blocks in inorganic crystal engineering, *Inorg. Chem.*, 40:1445-1453 (2001).

Muci et al., Practical palladium catalysts for C—N and C—O bond formation, *Top. Curr. Chem.*, 219:131-209 (2002).

Murahashi et al., Ruthenium-catalyzed cytochrome P-450 type oxidation of tertiary amines with alkyl hydroperoxides, *J. Am. Chem. Soc.*, 110:8256-8258 (1988).

Murata et al., 100% encapsulation of a hydrogen molecule into an open-cage fullerene derivative and gas-phase generation of H2@C60. *J. Am. Chem. Soc.*, 125:7152-7153 (2003).

Nishiyabu et al., Synthesis, structure, anion binding, and sensing by calix[4]pyrrole isomers, *J. Am. Chem. Soc.*, 128:11496-11504 (2006).

Panagopoulos et al., Toward the synthesis of new CTV derivatives, Abstracts of Papers, 235th ACS National Meeting, New Orleans, Apr. 6-10, 2008, Abstract.

Periasamy et al., Aryltitanium species through the reaction of N,N-dialkylarylamines with TiCl4: oxidative coupling, N-dealkylation, and reaction with eectrophiles, *J. Org. Chem.*, 65:3548-3550 (2000).

Redko et al., "Inverse Sodium Hydride": A crystalline salt that contains $H^+$ and $Na^-$, *J. Am. Chem. Soc.*, 124:5928-5929 (2002).

Rio et al., Water soluble supramolecular cyclotriveratrylene-[60]fullerene complexes with potential for biological applications. *Tetrahedron Lett.*, 43:4321-4324 (2002).

Sakurai et al., Chemistry of organosilicon compounds. 192. Preparation and reactions of dodecamethyl-3,4,7,8,11,12-hexasilacyclododeca-1,5,9-triyne, *Chem. Lett.*, 595-598 (1984).

Sanz et al., A route to regioselectively functionalized carbazoles, dibenzofurans, and dibenzothiophenes through anionic cyclization of benzyne-tethered aryllithiums, *J. Org. Chem.*, 71:6291-6294 (2006).

Schmidtchen, Artificial host molecules for the sensing of anions, *Top.Curr.Chem.*, 255:1-29 (2005).

Steed et al., Inclusion chemistry of cyclotriveratrylene and cyclotricatechylene, *Supramolecular Chemistry*, 7:37-45 (1996).

Tietze et al., Efficient methods for the synthesis of 2-hydroxyphenazine based on the Pd-catalyzed N-arylation of aryl bromides, *Org. Lett.*, 7:1549-1552 (2005).

Trepanier et al., 3,4-Dihydroisocarbostyril and 1,2,3,4-tetrahydroisoquinoline derivatives of ephedrine, *J. Med. Chem.*, 16:342-347 (1973).

Trost et al., Synthesis of (-)-D9-trans-tetrahydrocannabinol: Stereocontrol via mo-catalyzed asymmetric allylic alkylation reaction, *Org. Lett.*, 9:861-863 (2007).

Tsue et al., Exhaustively methylated azacalix[4]arene: preparation, conformation, and crystal structure with exclusively CH/p-controlled crystal architecture, *Org. Lett.*, 7:2165-2168 (2005).

Vale et al., Synthesis, structure, and conformation of aza[1n]metacyclophanes. *J. Org. Chem.*, 73:27-35 (2008).

Weisman et al., Selective N-protection of medium-ring triamines, *J. Chem. Soc. Chemical Communications*, 886-887 (1987).

Wolfe et al., Rational development of practical catalysts for aromatic carbon-nitrogen bond formation, *Acc. Chem. Res*, 31: 805-818 (1998).

Woodard et al., Perfluorophenyl derivatives of the elements. XXIX. The synthesis of some heterocycles of mercury, sulfur, selenium, tellurium, arsenic and antimony,*J. Organometallic Chem.*, 112: 9-19 (1976).

Yang et al., Diazido(1,4,7-tribenzyl-1,4,7-triazacyclononane-$\kappa^3 N$)copper(II), *Acta Crystallographica Section E*, 62:m2437-2438 (2006).

Yang et al., Palladium-catalyzed amination of aryl halides and sulfonates, *J. Organometallic Chem.*, 576: 125-146 (1999).

Zhang et al., Amino ccid promoted cul-catalyzed C—N bond formation between aryl halides and amines or N-containing heterocycles, *J. Org. Chem.*, 70:5164-5173 (2005).

Zhang et al., Noncovalent immobilization of C60 on gold surfaces by SAMs of cyclotriveratrylene derivatives, *Chemistry of Materials*, 17:2063-2068 (2005).

Zhang et al., Selective anion sensing by a tris-amide CTV derivative: $^1$H NMR titration, self-assembled monolayers, and impedance spectroscopy, *J. Am. Chem. Soc.*, 127:2006-2011 (2005).

Zhang et al., Supramolecular immobilization of fullerenes on gold surfaces: Receptors based on calix[n]arenes, cyclotriveratrylene (CTV) and porphyrins, *Comptes Rendus Chimie*, 9:1031-1037 (2006).

Zimmerman et al., Mesomorphism, isomerization, and dynamics in a new series of pyramidic liquid crystals, *J. Am. Chem. Soc.*, 124:15286-15301 (2002).

Collet, Comprehensive supramolecular chemistry, vol. 6, pp. 281-303, in Atwood et al.(eds.) *Comprehensive Supramolecular Chemistry*, Oxford, UK: Pergamon (1996).

Collet, Cyclotriveratrylenes and cryptophanes, *Tetrahedron*, 43:5725-5759 (1987).

Felder et al., A liquid crystalline supramolecular complex of C60 with a cyclotriveratrylene derivative, *Chemistry—A European Journal*, 6: 3501-3507 (2000).

Fuder et al., A novel route for converting aromatics into hydrogen via steam reforming. *Proceedings of the World Petroleum Congress*, 17: 395-403 (2002).

Harig et al., 2,3,6,7,10,11-hexamethoxytribenzotriquinacene: Synthesis, solid-state structure, and functionalization of a rigid analogue of cyclotriveratrylene, *Eur.J. Org. Chem*, 2381-2397 (2004).

Hartwig, Synthesis, structure, and reactivity of a palladium hydrazonato complex: a new type of reductive elimination reaction to form C—N bonds and catalytic arylation of benzophenone hydrazone, *Ang. Chem. Int. Ed.*, 37: 2090-2093 (1998).

Kopf et al., (2,3,7,8,12,13-Hexamethoxy-10,15-dihydro-5H-5,10,15-trithiatribenzo[a,d,g]cyclononene)trinitratorhodium(III) N,N-dimethylacetamide (1/3) $C_{24}H_{24}N_3O_{15}RhS_3 \cdot 3C_4H_9NO$ [1], *Crystal Structure Communications*, 8:1011-1016 (1979).

Liskamp et al., In *In From synthetic receptors toward synthetic antibodies*. 2003; pp. MEDI-160.

Pandey et al., Photooxidative SET [single-electron-transfer]-initiated N-demethylation of N,N'-dimethylanilines: mimicking the cytochrome P-450 type oxygenations, *Tetrahedron Lett.*, 31:1199-1202 (1990).

Von Deuten et al., Ligands with fixed coordination geometry. I. Bromo(2,3,7,8,12,13-hexamethoxy-10,15-dihydro-5H-5,10,15-trithia-tribenzo[a,d,g]cyclononene)copper(I)-acetone-water (1/1/1) $C_{24}H_{24}BrCuO_6S_3 \cdot C_3H_6O \cdot H_2O$, *Crystal Structure Communications*, 8:721-728 (1979).

Von Deuten et al., Cyclic ligands with fixed coordination geometry. Part III. Dichloro(2,3,7,8,12,13-hexamethoxy-10,15-dihydro-5H-5,10,15-trithiatribenzo[a,d,g]cyclononene)platinum(II)N,N-dimethylacetamide (2/3), $C_{24}H_{24}Cl_2O_6PtS_3 \cdot 1.5C_4H_9NO$, *Crystal Structure Communications*, 10:757-764 (1981).

Von Deuten et al., Organometalloidal compounds with o-phenylene substituents. V.2,3,7,8,12,13-Hexamethoxy-10,15-dihydro-5H-5,10,15-trithiatribenzo[a,d,g]cyclononene (saddle form)-benzene (2/1), $C_{24}H_{24}O_6S_3 \cdot 1/2 \, C_6H_6$. *Crystal Structure Communications*, 8: 569-575 (1979).

Von Deuten et al., Organometalloidal compounds with o-phenylene substituents. VII. Crystal and molecular structure of 10,15-dihydro-5H-5,10,15-trioxatribenzo[a,d,g]cyclononene (trimeric o-phenylene oxide) and its implications concerning preferred conformations of compounds $(arylene)_3X_3$. *Zeitschrift fuer Naturforschung, Teil B: Anorganische Chemie, Organische Chemie*, 36B:1526-1531 (1981).

Weiss et al., [b,e,h][1,4,7]trioxonin and tetra benzo [b,e,h,k][1,4,7,10]tetraoxadodecin *Zeitschrift fuer Naturforschung, Teil B: Anorganische Chemie, Organische Chemie, Biochemie, Biophysik, Biologie*, 29: 156-158 (1974).

Weiss et al., Organometalloidal compounds with o-phenylene substituents, IV. Synthesis of 2,3,7,8,12,13-hexamethoxytribenzo[b,e,h][1,4,7]trithiacyclononatriene. *Zeitschrift fuer Naturforschung, Teil B: Anorganische Chemie, Organische Chemie*, 34B:448-450 (1979).

* cited by examiner

SUPRAMOLECULAR SCAFFOLDS AND METHODS OF MAKING THE SAME

BACKGROUND

1. Field of the Disclosure

The disclosure relates generally to tribenzo-azacyclophanes and methods of making the same. More particularly, the disclosure is directed to tribenzo-1,4,7-triazacyclononane and related compounds, and to methods of making the same.

2. Brief Description of Related Technology

Cyclophanes are molecules having at least one aromatic group bridged by at least one hydrocarbon or substituted hydrocarbon chain. Many cyclophanes have a capacity to function as supramolecular scaffolds, and in addition, cyclophanes may recognize and bind specific molecules or ions. In host-guest chemistry, the supramolecular entity is commonly regarded as the host, and the bound ion or molecule comprises the guest. Anion-selective hosts, for example, are useful as sensors for environmentally important anion guests, such as nitrate and phosphate. In addition to their applications in analytical detection and sensing, supramolecular scaffolds are useful in fields such as materials science, catalysis, and drug delivery.

Cyclotriveratrylene (CTV) (Collet *Tetrahedron* 43:5725-5759 (1987)), for example, is a crown-shaped cyclophane scaffold that is readily prepared from the trimerization of veratryl alcohol in acid. CTV can bind a variety of small organic and organometallic guests within its bowl-shaped cleft, including DMSO, ethanol, chlorinated organics, xenon, lanthanides, organometallic complexes, and fullerenes such as $C_{60}$ and anionic $C_{70}$ dimers. CTV also has been found useful for selective anion sensing. In addition, derivatives of CTV and complexes of CTV with fullerenes are capable of forming liquid crystals.

One disadvantage of CTV is its poor water solubility. The solubility of CTV can be improved by appending polyethylene glycol substituents to CTV to form high molecular weight (>3000 to >6000 amu) derivatives. For many applications high molecular weight compounds can be unsuitable, and thus a need exists for water-soluble cyclophanes having lower molecular weights.

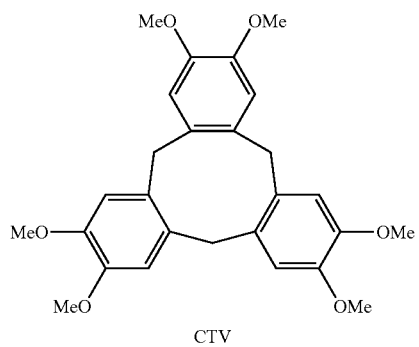

CTV

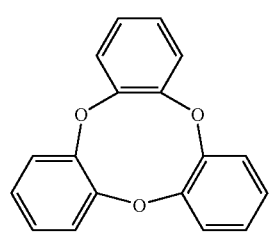

15

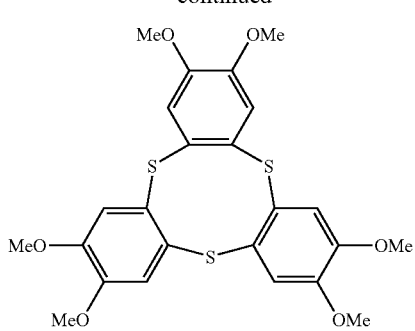

16

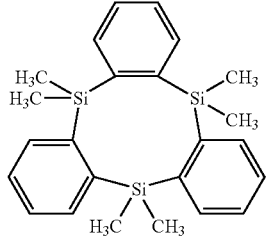

17

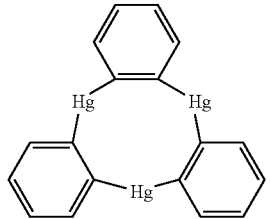

18

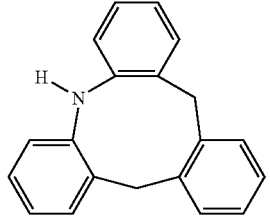

19

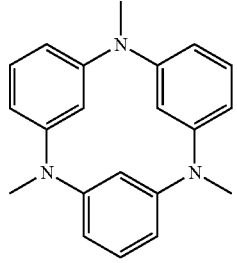

20

Several heteroatom derivatives of CTV are known. Trioxocyclononene 15 (Weiss et al. *Zeitschrift fuer Naturforschung, Teil B: Anorganische Chemie, Organische Chemie, Biochemie, Biophysik, Biologie,* 29:156-158 (1974), Von Deuten et al. *Zeitschrift fuer Naturforschung, Teil B: Anorganische Chemie, Organische Chemie* 36B:1526-1531(1981)) exhibits a crown-shaped stricture. Trithiacyclotriveratrylene 16 (Weiss et al. *Zeitschrift fuer Naturforschung, Teil B: Anorganische Chemie, Organische Chemie* 34B:448-450 (1979), Von Deuten et al. *Crystal Structure Communications* 8:569-575 (1979)) forms complexes with copper(I), rhodium(III), and platinum (II), and exists in a temperature- and solvent-dependent equilibrium of the crown and the saddle forms. The tris(dimethylsilyl) analog 17 (Sakurai et al. *Chemistry Letters*

595-598 (1984)) is conformationally mobile on the NMR time scale. The trimercury analog 18 (Woodard et al. *Journal of Organometallic Chemistry* 112:9-19 (1976)) is a planar Lewis acidic chelator that encapsulates Lewis basic halide anions. The tribenzo-1-azacyclononene derivative 19 (Zhang et al. *J. Org. Chem.* 70:5164-5173 (2005)) is theorized to have pharmacological activity as an anti-depressant. However, due to the presence of only a single amino group, compound 19 lacks the capability to chelate metals in the crown apex or to make carbon-capped orthoamide derivatives. Additionally, triaza[1$_3$]metacyclophane 20 (Ito et al. *J. Org. Chem.* 64:8236-8241 (1999)) lacks the ability to chelate metals or to make carbon-capped orthoamide derivatives due to the three-dimensional geometry enforced by meta substitution. Cyclophanes capable of chelating metals and orthoamide cyclophane derivatives are theorized to serve as new chelating ligands to modulate the properties of bound metals and advantageously bind guests with improved selectivity and/or affinity.

SUMMARY

The present disclosure is directed to compounds represented by formula (I) or a salt or metal complex thereof:

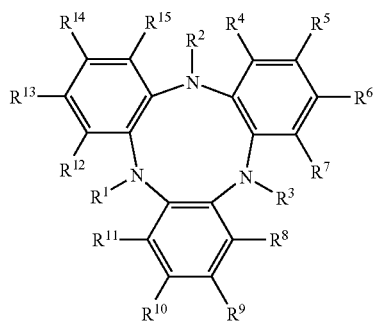

(I)

wherein:

$R^1$, $R^2$, and $R^3$ are each independently selected from the group consisting of: H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^1$; or $R^1$, $R^2$, and $R^3$ taken together are $CR^z$, B, or a metal;

$R^z$ is selected from the group consisting of Li, H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl;

$R^4$, $R^5$, $R^6$, $R^7$, $R^8$, $R^9$, $R^{10}$, $R^{11}$, $R^{12}$, $R^{13}$, $R^{14}$, and $R^{15}$ are each independently selected from the group consisting of: H, F, Cl, Br, I, —$NO_2$, —CN, —C(O)OH, —C(O)$OR^c$, —C(O)H, —C(O)$R^c$, —C(O)$NH_2$, —C(O)$NHR^c$, —C(O)$NR^cR^d$, —C(O)$SR^c$, —$NH_2$, —$NHR^c$, —$NR^cR^d$, —OH, —$OR^c$, —SH, —$SR^c$, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^2$;

$X^1$ and $X^2$ are each independently selected from the group consisting of: —C(O)OH, —C(O)$OR^a$, —C(O)H, —C(O)$R^a$, —C(O)$NH_2$, —C(O)$NHR^a$, —C(O)$NR^aR^b$, —C(O)$SR^a$, —$NH_2$, —$NHR^a$, —$NR^aR^b$, —OH, —$OR^a$, —SH, and —$SR^a$; and $R^a$, $R^b$, $R^c$, and $R^d$ are each independently selected from the group consisting of: optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl.

The disclosure is further directed to methods of making compounds represented by formula (I), including salts and complexes thereof, and methods of use as sensors, liquid crystals, catalyst scaffolds, and drug delivery systems.

DETAILED DESCRIPTION

Disclosed herein are tribenzo-azacyclophanes and methods of making the same. More specifically, the present disclosure is directed to tribenzo-1,4,7-triazacyclononane and derivatives thereof, and to methods of making the same.

Three synthetic routes are provided to obtain the disclosed compounds. The first approach provides the disclosed compounds via sequential N-arylation reactions. The second and third routes yield the disclosed compounds via a tandem N-arylation reaction.

As used herein, the term "alkyl" refers to straight chained and branched hydrocarbon groups, nonlimiting examples of which include methyl, ethyl, and straight chain and branched propyl and butyl groups. The term "alkyl" includes "bridged alkyl," i.e., a bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. Alkyl groups optionally can be substituted, for example, with hydroxy (—OH), oxo (=O), halo, aryl, heteroaryl, cycloalkyl, heterocycloalkyl, amino, nitro (—$NO_2$), and thio.

As used herein, the term "alicyclic" refers to straight chained and branched hydrocarbon groups containing at least one cycloalkyl group, which can be either saturated or unsaturated, but which is not aromatic.

As used herein, the term "cycloalkyl" refers to a cyclic hydrocarbon group, e.g., cyclopropyl, cyclobutyl, cyclohexyl, and cyclopentyl. "Heterocycloalkyl" is defined similarly as cycloalkyl, except the ring contains one to three heteroatoms independently selected from the group consisting of oxygen, nitrogen, and sulfur. Nonlimiting examples of heterocycloalkyl groups include piperdinyl, tetrahydrofuranyl, tetrahydropyranyl, dihydrofuranyl, and the like. Cycloalkyl and heterocycloalkyl groups can be saturated or partially unsaturated ring systems optionally substituted with, for example, one to three groups, independently selected from the group consisting of alkyl, alkylene-OH, —C(O)$NH_2$, —$NH_2$, —$NO_2$, oxo (=O), aryl, haloalkyl, halo, —OH and —SH. Heterocycloalkyl groups optionally can be further N-substituted with alkyl, hydroxyalkyl, alkylenearyl, or alkyleneheteroaryl.

As used herein, the term "alkenyl" is defined identically as "alkyl," except the group contains at least one carbon-carbon double bond.

As used herein, the term "alkynyl" is defined identically as "alkyl," except the group contains at least one carbon-carbon triple bond.

As used herein, the term "alkylene" refers to an alkyl group having a substituent. For example, the term "alkylene heterocycloalkyl" refers to an alkyl group substituted with a heterocycloalkyl group. The alkylene group is optionally substituted with one or more substituents previously listed as optional alkyl substituents.

As used herein, the term "alkenylene" is defined identically as "alkylene," except the group contains at least one carbon-carbon double bond.

As used herein, the term "alkynylene" is defined identically as "alkylene," except the group contains at least one carbon-carbon triple bond.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, —$OCF_3$, —$NO_2$, —CN, —NC, —OH, alkoxy, amino, —$CO_2H$, —$CO_2$-alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, —$OCF_3$, —$NO_2$, —CN, —NC, —OH, alkoxy, amino, —$CO_2H$, —$CO_2$-alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

As used herein, the term "alkali metal" refers to the metals of Group 1 of the periodic table. Exemplary alkali metals include, but are not limited to, Li, Na, and K.

As used herein, the term "transition metal" refers to the metals of Groups 3 to 12 of the periodic table. Exemplary transition metals include, but are not limited to, Zn, Cu, Co, Ni, Mo, and lanthanides, such as Gd.

As used herein, the term "halo" refers to the halogens of Group 17 of the periodic table, such as F, Cl, Br, and I.

As used herein, the term "amino" refers to —$NH_2$, —$NHR^a$, and —$NR^aR^b$, wherein $R^a$ and $R^b$ are as defined herein.

As used herein, the term "alkoxy" refers to —$OR^a$, wherein $R^a$ is as defined herein.

As used herein, the term "thio" refers to —SH, and —$SR^a$, wherein $R^a$ is as defined herein.

As used herein, the term "leaving group" refers to a functional group that detaches from a compound during a reaction. Exemplary leaving groups include, but are not limited to, —$NO_2$, —NCS, —SCN, —$N_3$, halo, acyloxy (—$OC(O)R^a$), alkoxy, aryloxy, —OH, —$OS(O)_2R^a$, —$OS(O)_2OR^a$, —OS$(O)OR^aOR^b$, —$NH_2$, —$NHR^a$, and —$NR^aR^b$, wherein $R^a$ and $R^b$ are as defined herein.

As used herein, the term "sulfonate leaving group" refers to —$OS(O)_2R^a$, wherein $R^a$ is as defined herein. Exemplary sulfonate leaving groups include, but are not limited to, fluorinated groups such as triflate and nonaflate, alkylated groups such as mesylate, and arylated groups such as tosylate and besylate.

Additionally, salts of the compounds disclosed herein also are included in the present disclosure and can be used in the methods disclosed herein. For example, an acid salt of a compound containing an amine or other basic group can be obtained, by reacting the compound with a suitable organic or inorganic acid, such as hydrogen chloride, hydrogen bromide, acetic acid, perchloric acid and the like. Examples of such salts include, but are not limited to, hydrochlorides, hydrobromides, sulfates, methanesulfonates, nitrates, maleates, acetates, citrates, fumarates, tartrates, succinates, benzoates and salts with amino acids such as glutamic acid. Salts of compounds containing a carboxylic acid or other acidic functional group can be prepared by reacting with a suitable base. Such salts include, but are not limited to, alkali metal salts (e.g., sodium and potassium), alkaline earth metal salts (e.g., calcium and magnesium), aluminum salts ammonium salts, and salts of organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

The present disclosure is directed to a compound of formula (I) or a salt or metal complex thereof:

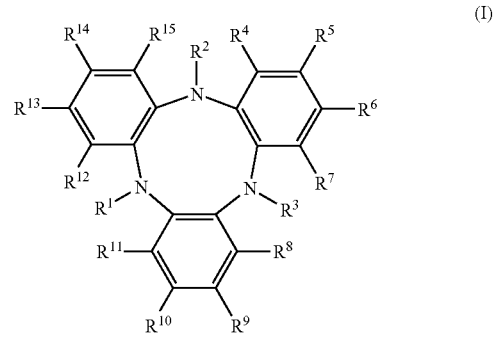

(I)

wherein:

$R^1$, $R^2$, and $R^3$ are each independently selected from the group consisting of: H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^1$; or $R^1$, $R^2$, and $R^3$ taken together are $CR^z$, B, or a metal;

$R^z$ is selected from the group consisting of Li, H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl;

$R^4$, $R^5$, $R^6$, $R^7$, $R^8$, $R^9$, $R^{10}$, $R^{11}$, $R^{12}$, $R^{13}$, $R^{14}$, and $R^{15}$ are each independently selected from the group consisting of: H, F, Cl, Br, I, —$NO_2$, —CN, —C(O)OH, —C(O)$OR^c$, —C(O)H, —C(O)$R^c$, —C(O)$NH_2$, —C(O)$NHR^c$, —C(O)$NR^cR^d$, —C(O)$SR^c$, —$NH_2$, —$NHR^c$, —$NR^cR^d$, —OH, —$OR^c$, —SH, —$SR^c$, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^2$;

$X^1$ and $X^2$ are each independently selected from the group consisting of: —C(O)OH, —C(O)O$R^a$, —C(O)H, —C(O)$R^a$, —C(O)NH$_2$, —C(O)NH$R^a$, —C(O)N$R^a R^b$, —C(O)S$R^a$, —NH$_2$, —NH$R^a$, —N$R^a R^b$, —OH, —O$R^a$, —SH, and —S$R^a$; and $R^a$, $R^b$, $R^c$, and $R^d$ are each independently selected from the group consisting of: optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl.

The present disclosure is further directed to the compound of formula (I) or a salt or metal complex thereof wherein $R^4$, $R^5$, $R^6$, $R^7$, $R^8$, $R^9$, $R^{10}$, $R^{11}$, $R^{12}$, $R^{13}$, $R^{14}$, and $R^{15}$ are each independently selected from the group consisting of: H, F, Cl, Br, and I.

The present disclosure also is directed to a compound of formula (II) or a salt or metal complex thereof:

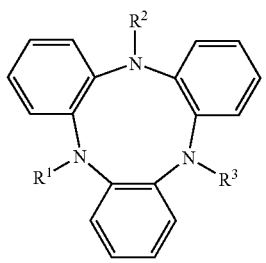

(II)

wherein:

$R^1$, $R^2$, and $R^3$ are each independently selected from the group consisting of: H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^1$; or $R^1$, $R^2$, and $R^3$ taken together are C$R^z$, B, or a metal;

$R^z$ is selected from the group consisting of Li, H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl;

$X^1$ is selected from the group consisting of: —C(O)OH, —C(O)O$R^a$, —C(O)H, —C(O)$R^a$, —C(O)NH$_2$, —C(O)NH$R^a$, —C(O)N$R^a R^b$, —C(O)S$R^a$, —NH$_2$, —NH$R^a$, —N$R^a R^b$, —OH, —O$R^a$, —SH, and —S$R^a$; and $R^a$ and $R^b$ are each independently selected from the group consisting of: optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl.

The present disclosure is further directed to a compound of formula (II) or a salt or metal complex thereof, wherein:

$R^1$, $R^2$, and $R^3$ are each independently selected from the group consisting of: H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^1$;

$X^1$ is —C(O)OH, —C(O)O$R^a$, —C(O)H, —C(O)$R^a$, —C(O)NH$_2$, —C(O)NH$R^a$, —C(O)N$R^a R^b$, —C(O)S$R^a$, —NH$_2$, —NH$R^a$, —N$R^a R^b$, —OH, —O$R^a$, —SH or —S$R^a$; and $R^a$ and $R^b$ are each independently selected from the group consisting of: optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl.

The present disclosure is further directed to a compound of formula (III) or a salt or metal complex thereof:

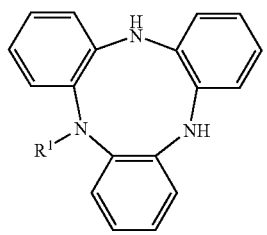

(III)

wherein:

$R^1$ is H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, or $C_1$ to $C_{20}$ alkylene-$X^1$;

$X^1$ is —C(O)OH, —C(O)O$R^a$, —C(O)H, —C(O)$R^a$, —C(O)NH$_2$, —C(O)NH$R^a$, —C(O)N$R^a R^b$, —C(O)S$R^a$, —NH$_2$, —NH$R^a$, —N$R^a R^b$, —OH, —O$R^a$, —SH, or —S$R^a$; and $R^a$ and $R^b$ are each independently selected from the group consisting of: optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl.

The present disclosure also is directed to a compound having a formula:

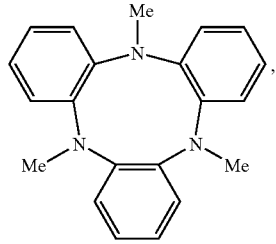
(XXI)

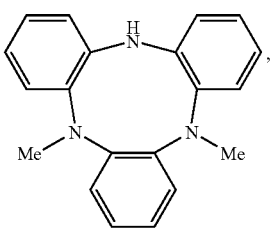
(IV)

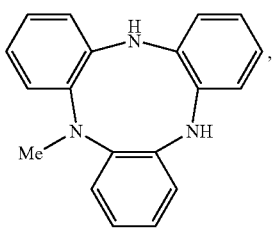
(XXII)

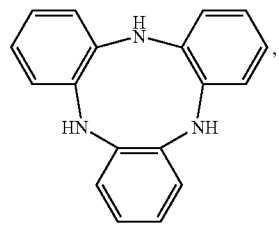
(V)

or a salt or metal complex thereof.

N-alkylated derivatives of the compound of formula (V) can provide improved properties (e.g., increased water solubility) and/or improved functionality (e.g., functional groups capable of binding to surfaces, reacting with solid-phase resins, or serving as an additional chelating unit for a bound metal). Exemplary N-alkylated derivatives include, but are not limited to: the compounds of formulae (VI), (VII), and (VIII). A variety of known methods can be used to synthesize N-alkylated derivatives of (V). The compound of formula (VI) can be obtained, for example, by reacting (V) with γ-bromobutanoic acid in dimethylformamide (DMF) in the presence of potassium carbonate as a base.

(VI)

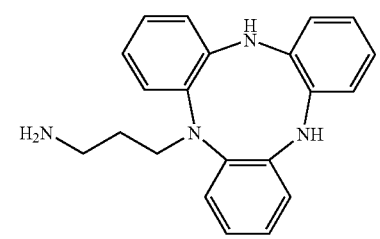
(VII)

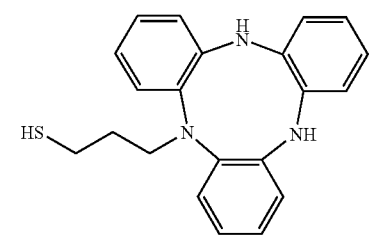
(VIII)

To prepare the compound of formula (VII), for example, compound (V) can be alkylated with the t-butylcarbamate (Boc)-protected derivative of 1-amino-3-chloropropane in DMF in the presence of potassium carbonate as a base, followed by subsequent removal of the Boc protecting group with trifluoroacetic acid. Compound (VII) can be further processed to produce a variety of products. Reaction of (VII) with the chloromethyl functionality of Merrifield resin in DMF in the presence of diisopropylethylamine, for example, can yield a resin-bound derivative of (VII). In addition, the ammonium form of compound (VII) can be electrostatically bound to silica surfaces.

The compound of formula (VIII) can be prepared, for example, by alkylation of compound (V) with 3-mercaptobromopropane. The resulting thiol of (VIII) can be used to bind the compound to surfaces.

Other suitable reaction conditions for the above reactions will be readily apparent to the skilled practitioner. A variety of additional N-alkylated derivatives also will be apparent to the skilled practitioner.

Compound (V) can exist in a crown-shaped conformation. The above N-alkylated derivatives of compound (V) modify the apex of the crown, thereby leaving the concave surface of the crown ("the bowl") available for recognition by guests. In contrast, modification of the base of the crown can limit access to the concave surface of the crown. Although such modifications of the base can exclude certain guests, the limited access to the bowl of compound (V) also can contribute to enhanced specificity and/or affinity for other guest molecules and/or ions.

N-alkylated derivatives of the compound of formula (V) also include compounds of formulae (X) and (XA). The compound of formula (X) can be obtained, for example, by reacting (V) with N,N-dimethylformamide dimethyl acetal. Accordingly, derivatives of (X) having apical substituents in place of the apical hydrogen atom can be prepared by using the appropriate dimethyl ketal. Such derivatives can display improved properties (e.g., increased water solubility) and/or improved functionality (e.g., functional groups capable of binding to surfaces or reacting with solid-phase resins). Alternatively, compound (X) can be further processed to produce a variety of products. Deprotonation of the apical hydrogen of (X) with a strong base such as butyl lithium can provide access to various apical substituents, for example, via the lithiated derivative (XA). The carbanion of (X) resulting from deprotonation can be reacted with bromine, for example, to produce an apical carbon radical that can be exposed to a variety of functional groups including, but not limited to alkenes.

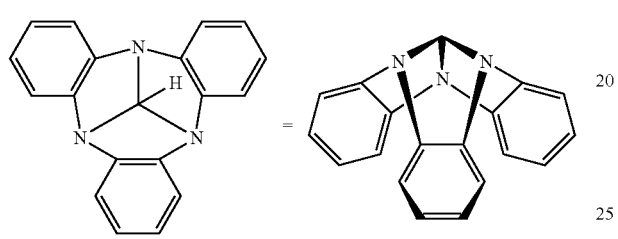

(X)

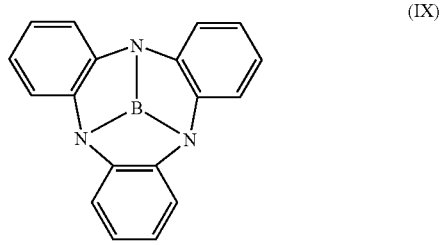

(XA)

Derivatives of compound (V) also include compounds having a formula (IX).

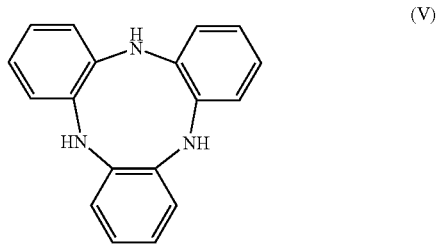

(IX)

The compounds disclosed herein can form complexes with various metals, inorganic and organic ions, and inorganic and organic molecules. Complexes of the disclosed compounds with lanthanides such as gadolinium can be useful, for example, as magnetic resonance imaging agents. Other suitable metals for the formation of complexes include, but are not limited to: alkali metals such as lithium, sodium, and potassium; transition metals such as zinc, copper, cobalt, nickel, and molybdenum; and combinations thereof.

The present disclosure is directed to methods of preparing 10,15-dihydro-5H-tribenzo[b,e,h][1,4,7]triazonine (formula (V)) and derivatives thereof. The methods comprise:

(i) subjecting a compound of formula (XI) to conditions sufficient to form a compound of formula (XII):

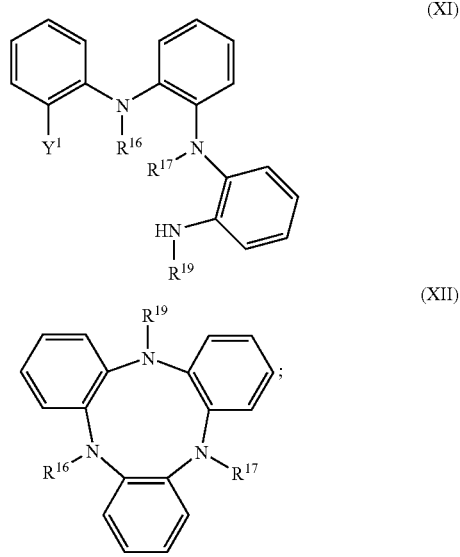

wherein $Y^1$ is F, Cl, Br, I, or a sulfonate leaving group;

$R^{16}$ and $R^{17}$ are each independently selected from the group consisting of: optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^3$;

$R^{19}$ is selected from the group consisting of: H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^4$;

$X^3$ and $X^4$ are each independently selected from the group consisting of: —C(O)OH, —C(O)OR$^a$, —C(O)H, —C(O)R$^a$, —C(O)NH$_2$, —C(O)NHR$^a$, —C(O)NR$^a$R$^b$, —C(O)SR$^a$, —NH$_2$, —NHR$^a$, —NR$^a$R$^b$, —OH, —OR$^a$, —SH, and —SR$^a$;

$R^a$ and $R^b$ are each independently selected from the group consisting of: optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl; and (ii) subjecting a compound of formula (XII) to conditions sufficient to form a compound of formula (V):

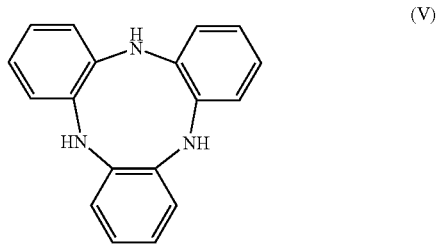

(V)

The conditions sufficient to form a compound of formula (XII) can comprise admixing the compound of formula (XI), a catalyst, and a base. More specifically compound (XII) can be formed from compound (XI) by a carbon-nitrogen bond-forming reaction, for example, a palladium catalyzed cross-coupling reaction such as a Buchwald-Hartwig reaction. Exemplary groups for $R^{19}$ include, but are not limited to, primary alkyl groups. Suitable examples of primary alkyl groups include, but are not limited to, methyl, ethyl, benzyl, and substituted benzyl.

Compound (V) can be formed from compound (XII), for example, by a dealkylation (or dearylation) reaction.

The methods in accordance with the present disclosure further comprise:

subjecting a compound of formula (XIII) to conditions sufficient to form a compound of formula (XI):

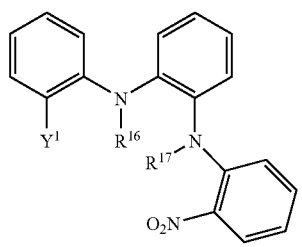

(XIII)

Compound (XI) can be formed from compound (XIII), for example, by a reduction reaction to form compound (XI) having $R^{19}$ equal to hydrogen. Compound (XI) having $R^{19}$ different from hydrogen can be obtained from compound (XI) having $R^{19}$ equal to hydrogen, for example, by alkylation or reductive amination. Suitable conditions for alkylation include reaction with alkyl halides, such as methyl bromide or ethyl iodide. Suitable conditions for reductive amination include reaction with a mixture comprising an aldehyde (e.g., benzaldehyde) and a reducing agent (e.g., sodium cyanoborohydride).

The methods in accordance with the present disclosure further comprise:

subjecting a compound of formula (XIV) in the presence of a compound of formula $R^{17}$—Z to conditions sufficient to form a compound of formula (XIII):

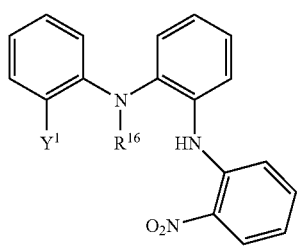

(XIV)

wherein Z is a leaving group.

Compound (XIII) can be formed from compound (XIV), for example, by an alkylation (or arylation) reaction.

The methods in accordance with the present disclosure further comprise:

subjecting a mixture comprising a compound of formula (XV) and a compound of formula (XVA) to conditions sufficient to form a compound of formula (XIV):

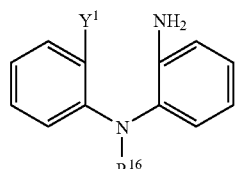

(XV)

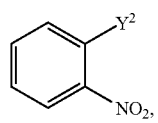

(XVA)

wherein $Y^2$ is F, Cl, Br, I, or a sulfonate leaving group, with the proviso that $Y^2$ is different from $Y^1$.

The conditions sufficient to form a compound of formula (XIV) can comprise admixing the compound of formula (XV), the compound of formula (XVA), a catalyst, and a base. More specifically, compound (XIV) can be formed from compound (XV) by a carbon-nitrogen bond-forming reaction, for example, a palladium catalyzed cross-coupling reaction such as a Buchwald-Hartwig reaction.

The methods in accordance with the present disclosure further comprise:

subjecting a compound of formula (XVI) to conditions sufficient to form a compound of formula (XV):

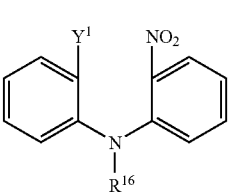

(XVI)

Compound (XV) can be formed from compound (XVI), for example, by a reduction reaction.

The methods in accordance with the present disclosure further comprise:

subjecting a compound of formula (XVII) in the presence of a compound of formula $R^{16}$—Z to conditions sufficient to form a compound of formula (XVI):

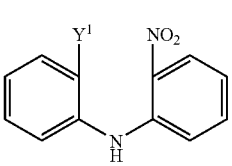

(XVII)

wherein Z is a leaving group.

Compound (XVI) can be formed from compound (XVII), for example, by an alkylation (or arylation) reaction.

The methods in accordance with the present disclosure further comprise:

subjecting a mixture comprising a compound of formula (XVIII) and a compound of formula (XIX) to conditions sufficient to form a compound of formula (XVII):

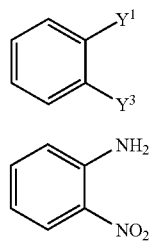

wherein Y³ is F, Cl, Br, I, or a sulfonate leaving group, with the proviso that Y³ is different from Y¹.

The conditions sufficient to form a compound of formula (XVII) can comprise admixing the compound of formula (XVIII), the compound of formula (XIX), a catalyst, and a base. More specifically, compound (XVII) can be formed from a mixture comprising compound (XVIII) and compound (XIX) by a carbon-nitrogen bond-forming reaction, for example, a palladium catalyzed cross-coupling reaction such as a Buchwald-Hartwig reaction.

The present disclosure is further directed to a method of preparing a derivative of 10,15-dihydro-5H-tribenzo[b,e,h][1,4,7]triazonine comprising:

subjecting a compound of formula (XIIA) in the presence of a compound of formula $R^{18}$—Z to conditions sufficient to form a compound of formula (XX):

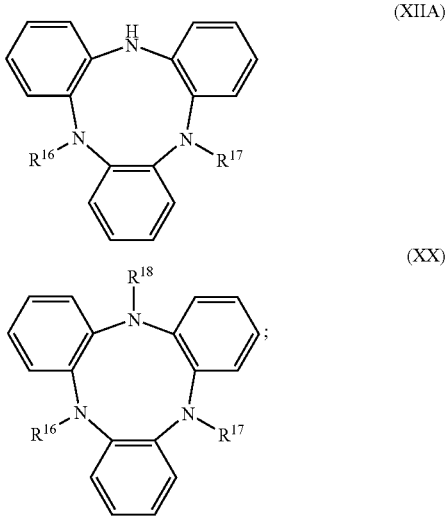

wherein $R^{16}$, $R^{17}$, and $R^{18}$ are each independently selected from the group consisting of: optionally substituted linear or branched $C_1$ to $C_{20}$ alkyl; optionally substituted linear or branched $C_2$ to $C_{20}$ alkenyl; optionally substituted linear or branched $C_2$ to $C_{20}$ alkynyl; optionally substituted $C_3$ to $C_{20}$ alicyclic; aryl; heteroaryl; optionally substituted $C_1$ to $C_{20}$ alkylene-aryl; optionally substituted $C_1$ to $C_{20}$ alkylene-heteroaryl; and $C_1$ to $C_{20}$ alkylene-X;

X is —C(O)OH, —C(O)OR$^a$, —C(O)H, —C(O)R$^a$, —C(O)NH$_2$, —C(O)NHR$^a$, —C(O)NR$^a$R$^b$, —C(O)SR$^a$, —NH$_2$, —NHR$^a$, —NR$^a$R$^b$, —OH, —OR$^a$, —SH, or —SR$^a$;

R$^a$ and R$^b$ are each independently selected from the group consisting of: optionally substituted linear or branched $C_1$ to $C_{20}$ alkyl; optionally substituted linear or branched $C_2$ to $C_{20}$ alkenyl; optionally substituted linear or branched $C_2$ to $C_{20}$ alkynyl; optionally substituted $C_3$ to $C_{20}$ alicyclic; aryl; heteroaryl; optionally substituted $C_1$ to $C_{20}$ alkylene-aryl; and optionally substituted $C_1$ to $C_{20}$ alkylene-heteroaryl; and Z is a leaving group.

Compound (XX) can be formed from compound (XIIA), for example, by an alkylation (or arylation) reaction.

In accordance with the methods disclosed herein, the preparation of formula (V) and derivatives thereof involves the formation of one or more carbon-nitrogen (C—N) bonds. For example, formation of compounds of formula (XII) from compounds of formula (XI) involves the formation of an intramolecular C—N bond, and formation of compounds of formula (XIV) from compounds of formula (XV) involves the formation of an intermolecular C—N bond. Additionally, formation of compounds of formula (XVIII) from a mixture of compounds of formulae (XVIII) and (XIX), for example, involves the formation of an intermolecular C—N bond.

C—N bonds can be formed by various known means, for example, by palladium-catalyzed cross-coupling reactions, such as Buchwald-Hartwig reactions and Goldberg reactions. Buchwald-Hartwig reactions generally involve the coupling of an aryl halide or aryl halide equivalent (e.g., an aryl triflate) and an amine in the presence of a catalyst and a base to form a C—N bond. Typically, the catalyst comprises palladium. Typical solvents include toluene, xylene, 1,4-dioxane, and tetrahydrofuran (THF).

Palladium catalysts typically are Pd(II) salts, but can also be Pd(0) or Pd(IV). The palladium catalysts can comprise coordinating ligands. The coordinating ligands can affect the reactivity and yield of the coupling reaction. The choice of ligand will be readily ascertainable by a skilled practitioner. Suitable coordinating ligands include, but are not limited to: phosphine ligands such as triphenylphosphine (PPh$_3$), diphenylmethylphosphine, phenyldimethylphosphine, 1,4-bis(diphenylphosphino)butane, 1,3-bis(diphenylphosphino)propane, 1,2-bis (diphenylphosphino)ethane, 1,1'-bis(diphenylphosphino)ferrocene (dppt), 2,2'-bis(diphenylphosphino)-1,1'-binaphthyl (BINAP), tricyclohexylphosphine, o-tolyl-phosphine, 2-(di-tert-butylphosphino)biphenyl, 2-(dicyclohexylphosphino)biphenyl, 2-(dicyclohexylphosphino)-2'-(N,N-dimethylamino)biphenyl, and tri(t-butyl)phosphine; dibenzylideneacetone (dba); chloride; acetate; acetylacetonate (acac); benzonitrile; and 1,3-bis(2,4,6-trimethylphenyl)imidazolium chloride.

Various suitable bases are known, and the choice of base is readily ascertainable by a skilled practitioner. Exemplary bases include, but are not limited to: Cs$_2$CO$_3$, K$_2$CO$_3$, LiN(SiMe$_3$)$_2$, K$_3$PO$_4$, KOtBu, and NaOtBu.

In accordance with the methods disclosed herein, the preparation of formula (V) and derivatives thereof involves the dealkylation (or dearylation) of one or more N-substituted amino groups. For example, formation of a compound of formula (V) from compounds of formula (XII) involves the dealkylation of two N-substituted amino groups.

Dealkylation (or dearylation) of N-substituted amino groups can be performed using a variety of conditions. Suitable conditions include, but are not limited to: HCl; HBr; Krapcho conditions (e.g., heating in the presence of LiCl, NaCl, KCl, LiBr, NaBr, KBr, LiI, NaI, and/or KBr in a solvent such as N,N-dimethylacetamide (DMAC), N,N-dimethylformamide (DMF), and/or DMF-water); chloroformates such as methyl chloroformate, ethyl chloroformate, and benzyl chloroformate; Lewis acids such as TiCl$_4$, BCl$_3$, BBr$_3$, ZnBr$_2$, SnCl$_2$, and AlCl$_3$; oxidative methods; photochemical methods (e.g., photolysis in methanol containing aqueous NaOH or aqueous KOH and an electron acceptor such as dicyanonaphthalene); and LiAlH$_4$.

In accordance with the methods disclosed herein, the preparation of formula (V) and derivatives thereof involves the reduction of one or more nitro groups to amino groups in the presence of a halide or halide equivalent. For example, formation of compounds of formula (XIX) from compounds of formula (XIII) involves the reduction of a nitro group to an amino group in the presence of a chloro group. Additionally, formation of compounds of formula (XV) from compounds of formula (XVI), for example, involves the reduction of a nitro group to an amino group in the presence of a chloro group.

Although a variety of conditions can be used to reduce a nitro group to an amino group, many such reduction conditions also convert halides or halide equivalents to hydrogen atoms. According to the methods disclosed herein, reduction of a reactant comprising a nitro group and a halide or halide equivalent is carried out under conditions such that the major product of the reaction comprises an amino group and a halide or halide equivalent. Suitable conditions for the reduction of the compounds disclosed herein include, but are not limited to potassium borohydride in the presence of copper (I) chloride.

In accordance with the methods disclosed herein, the preparation of formula (V) and derivatives thereof involves the N-substitution of one or more secondary amino groups with alkyl (or aryl) groups. For example, formation of compounds of formula (XIII) from compounds of formula (XIV) involves the alkylation (or arylation) of an amino group. Additionally, formation of compounds of formula (XVI) from compounds of formula (XVII), formation of compounds of formula (XX) from compounds of formula (XII), and formation of compounds of formula (II) from compounds of formula (V), for example, involve the alkylation (or arylation) of an amino group.

N-substitution can be performed using a variety of conditions. An amino group can be alkylated with a methyl group (methylated), for example, using Me$_2$SO$_4$ or methyl iodide in the presence of a base. Similarly, an amino group can be alkylated with an ethyl group (ethylated), for example, using ethyl iodide in the presence of a base.

The compounds of formulae (I) to (X), (XII), and (XX) of the present disclosure can be further functionalized at open sites (e.g., hydrogens) on the aromatic rings. A variety of aryl substitution reactions are known to the skilled practitioner. Exemplary reactions include, but are not limited to: chlorination using sodium hypochlorite; chlorination using sulfuryl chloride and phosphorous pentachloride; and Friedel-Crafts alkylation (e.g., ethylation using ethyl chloride in the presence of aluminum trichloride).

The invention can be better understood by reference to the following examples which are not intended to be limiting, but only exemplary of specific embodiments of the disclosure.

EXAMPLES

Example 1

Preparation of 10,15-Dihydro-5H-tribenzo[b,e,h][1,4,7]triazonine Using a Sequential N-arylation Route Scheme 1 outlines the transformation of (2'-chlorophenyl)-(2-nitrophenyl)amine (Compound 1) to 10,15-dihydro-5H-tribenzo[b,e,h][1,4,7]triazonine (formula (V)) in 8 synthetic steps via a sequential N-arylation sequence. Compound 1 was obtained in nearly quantitative yield via a Buchwald-Hartwig reaction of 2-nitroaniline with 2-bromochlorobenzene in the presence of catalytic Pd$_2$(dba)$_3$ (dba=dibenzylidene acetone), 2,2'-bis(diphenylphosphino)-1,1'-binaphthalene (BINAP), and cesium carbonate. Alkylation with dimethyl sulfate in the presence of KOH afforded N-methylated compound 2 in quantitative yield. Reduction of the nitro group of compound 2 was affected in quantitative yield and without concurrent dechlorination. Specifically, compound 2 was treated with potassium borohydride in the presence of copper (I) chloride to obtain the corresponding aniline (compound 3). Buchwald-Hartwig reaction of compound 3 with o-iodonitrobenzene gave the triaryl compound 4 as a red solid. Methylation of compound 4 with potassium hydride and methyl iodide gave the N,N'-dimethylated compound 5 as a yellow powder in 86% yield. Reduction of the nitro group of compound 5 was accomplished using potassium borohydride in the presence of copper (I) chloride to obtain the corresponding aniline (compound 6) as a dark yellow oil. Reductive amination of compound 6 with benzaldehyde in the presence of sodium triacetoxyborohydride and acetic acid furnished compound 7.

Buchwald-Hartwig cyclization of compound 7 using, for example, Pd$_2$(dba)$_3$, BINAP, and cesium carbonate affords the cyclic dialkyl compound 8. Dealkylation of compound 8 using HCl, HBr, Krapcho conditions, chloroformate methods, Lewis acids, oxidative methods, photochemical methods, or lithium aluminum hydride provides formula (V).

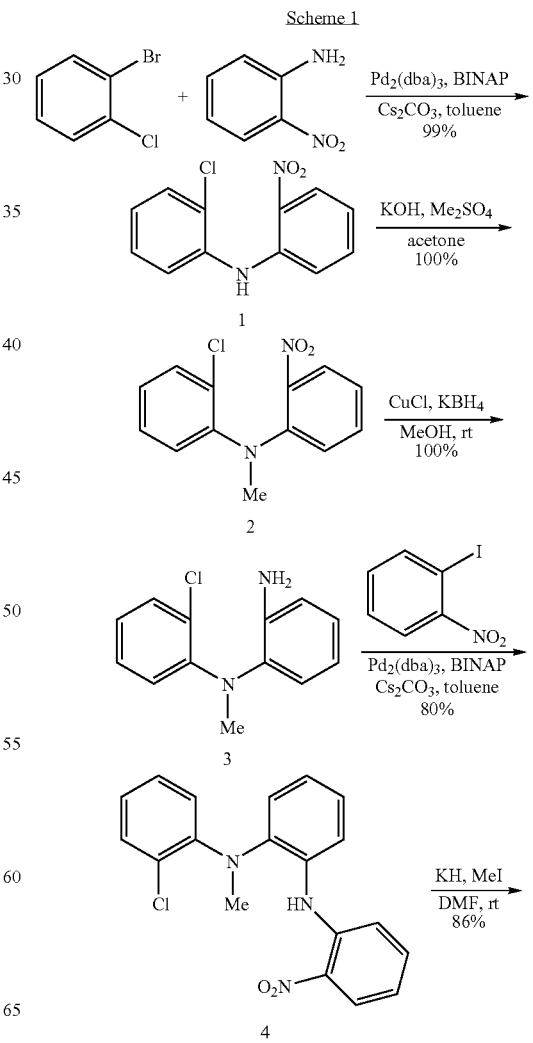

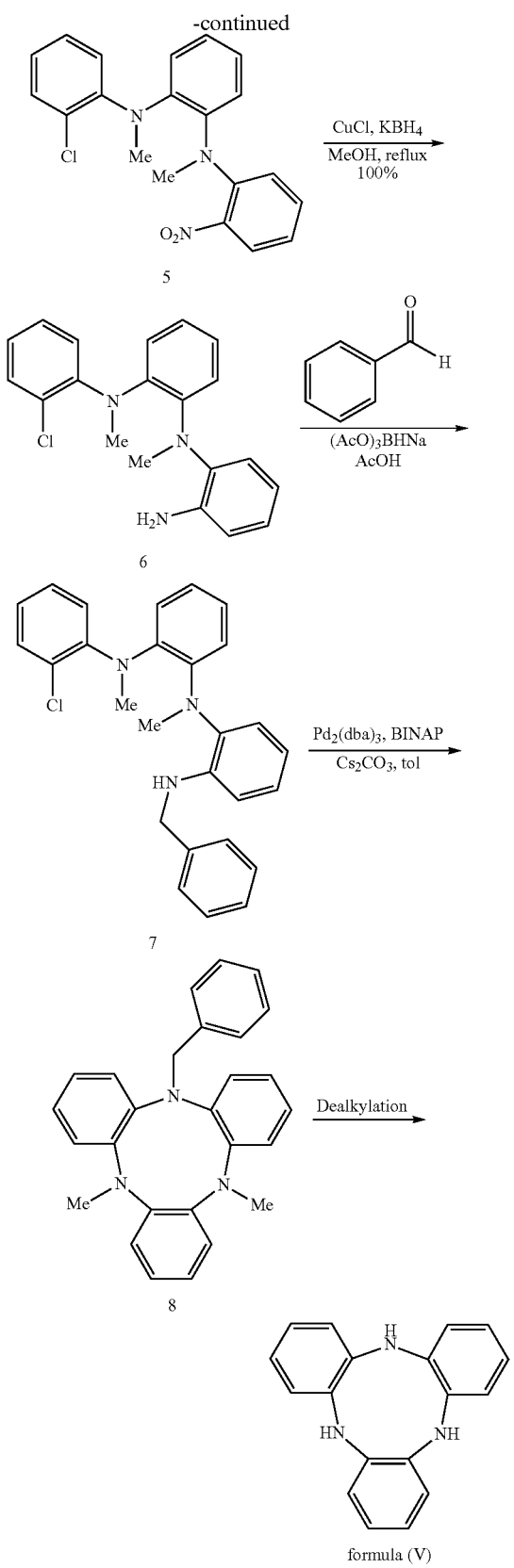

Synthesis of (2-chlorophenyl)-(2-nitrophenyl)amine (Compound 1). Compound 1 was prepared according to the general procedures outlined by Tietze et al. ("Efficient Methods for the Synthesis of 2-Hydroxyphenazine Based on the Pd-Catalyzed N-Arylation of Aryl Bromides." *Org. Lett.* 2005, 7. 1549-1552). The solvent was removed under vacuum and no further purification was needed to give the product as an orange solid. (1.24 g, 99% yield).

Synthesis of 2-chloro-N-methyl-N-(2-nitrophenyl)aniline (Compound 2). Compound 1 (1.25 g, 5 mmol) was stirred at room temperature in acetone (16 mL). To this, KOH (1.23 g, 22 mmol) was added. The mixture stirred at reflux for 1 h. To this, $Me_2SO_4$ (2.18 mL, 23 mmol) was added dropwise over 10 min. The mixture stirred at reflux for 1 h. The reaction was allowed to cool to room temperature. 10M NaOH was added and the reaction was stirred at room temperature. The mixture was quenched with 10 mL $H_2O$ and extracted 3 times with 10 mL dichloromethane. Organic layers were combined and dried over $Na_2SO_4$. Solvent was removed under vacuum and the mixture was placed in an 80° C. oil bath under vacuum to remove excess $Me_2SO_4$. No further purification was needed to give the product as a black oil (1.31 g, 100% yield). $^1$H NMR (300 MHz, $CDCl_3$) δ 7.68 (1H, dd, J=8.1, 1.5 Hz), 7.54 (1H, ddd, J=8.7, 7.3, 1.7 Hz), 7.42 (1H, dd, J=7.8, 1.5 Hz), 7.19 (1H, dd, J=7.7, 1.7 Hz), 7.14-7.11 (2H, m), 7.06 (1H, dd, J=7.7, 1.9 Hz), 7.0 (1H, ddd, J=8.2, 7.3, 1.1 Hz); $^{13}$C (75 MHz, $CDCl_3$) δ 145.0 (q), 143.0 (q), 133.2 (t), 131.3 (t), 130.9 (q), 128.7 (q), 127.9 (t), 126.7 (t), 126.2 (t), 125.9 (t), 120.8 (t), 120.6 (t), 41.1.

Synthesis of $N^1$-(2-chlorophenyl)-$N^1$-methylbenzene-1,2-diamine (Compound 3). Compound 2 (0.121 g, 0.46 mmol) was stirred at room temperature in MeOH (4.6 mL). To this, CuCl (0.137 g, 1.38 mmol) was added and mixture stirred at room temperature for 5-10 min. $KBH_4$ (0.174 g, 3.22 mmol) was added in portions. The reaction was stirred at room temperature until the solution became clear. The reaction was quenched with deionized $H_2O$ and extracted 3 times with 15 mL of a 90:10 mixture of ethyl acetate:dichloromethane. The organic layers were combined and dried over $Na_2SO_4$. The solvent was removed to give a brownish-black solid (107 mg, 100% yield). $^1$H NMR (300 MHz, $CDCl_3$) δ 7.32 (1H, dd, J=7.8, 1.4 Hz), 7.25 (1H, dd, J=7.3, 1.7 Hz), 7.22 (1H, dd, J=7.1, 1.7 Hz), 7.16, (1H, dd, J=8.0, 1.6 Hz), 7.00-6.95 (2H, m), 6.76 (1H, ddd, J=9.3, 7.7, 1.4 Hz), 6.67 (1H, ddd, J=8.9, 7.6, 1.5 Hz); $^{13}$C (75 MHz, $CDCl_3$) δ 147.6 (q), 142.2 (q), 136.9 (q), 130.7 (t), 130.68 (q), 127.4 (t), 125.5 (t), 123.6 (t), 121.9 (t), 118.6 (t), 115.8 (t), 41.1.

Synthesis of $N^1$-(2-chlorophenyl)-$N^1$-methyl-$N^2$-(2-nitrophenyl)benzene-1,2-diamine (Compound 4). Compound 3 (0.842 g, 3.62 mmol), o-iodonitrobenzene (1.35 g, 5.43 mmol), $Pd_2(dba)_3$ (0.104 g, 5% mol), BINAP (0.170 g, 7.5%), $Cs_2CO_3$ (2.35 g, 7.42 mmol) and 12 mL of toluene were placed in a pressure tube. The mixture was purged with argon at room temperature for 15 min. The tube was sealed and placed in an oil bath at 80-90° C. for 30 h. When thin-layer chromatography (TLC) showed consumption of compound 3, the reaction mixture was filtered through silica gel with a 90:10 mixture of ethyl acetate:dichloromethane. The solvent was then removed under vacuum. The product was purified by column chromatography on silica gel using a 8:92 mixture of methyl chloride:petroleum ether as the eluent to afford the product as a red crystalline solid (0.785 g, 80% yield). $^1$H NMR (300 MHz, $CDCl_3$) δ 9.03 (1H, bs), 8.07 (1H, dd, J=8.7, 1.5 Hz), 7.32-7.19 (4H, m), 7.12-6.99 (5H, m), 6.90 (1H, ddd, J=8.0, 6.9, 2.2 Hz), 6.68 (1H, ddd, J=8.4, 6.9, 1.2 Hz), 3.16 (3H, s); $^{13}$C (75 MHz, $CDCl_3$) δ 147.2 (q), 145.1 (q), 142.4 (q), 135.2 (t), 131.6 (q), 130.7 (t), 129.5 (q), 127.4 (t), 126.5 (t), 126.5 (t), 126.0 (t), 124.8 (t), 124.0 (t), 123.2 (t), 121.7 (t), 117.0 (t), 115.8 (t), 40.6.

Synthesis of $N^1$-(2-chlorophenyl)-$N^1$,$N^2$-dimethyl-$N^2$-(2-nitrophenyl)benzene-1,2-diamine (Compound 5). Compound 4 (0.405 g, 1.14 mmol) was dissolved in 4 mL of dimethylformamide (DMF) and added to KH (0.46 g, 3.42 mmol). The mixture was stirred at room temperature for 10 min. To this, MeI (0.4 mL, 5.7 mmol) was added dropwise. The reaction was allowed to stir at room temperature for 30 min. The reaction was then quenched with deionized $H_2O$ and extracted 3 times with 15 mL dichloromethane. The organic layers were combined and washed 3 times with 15 mL of $H_2O$, and 3 times with 15 mL of brine. The organic layers were dried with $MgSO_4$, and solvent was removed under reduced pressure to give the desired product as a yellow powder without further purification (0.362 g, 86% yield). $^1$H NMR (300 MHz, $CDCl_3$) δ 7.63 (1H, dd, J=8.0, 1.7 Hz), 7.36 (1H, ddd, J=8.8, 7.3, 1.8 Hz), 7.29-7.19 (2H, m), 7.12 (1H, dd. J=8.2, 1.7 Hz), 7.07-6.92 (5H, m), 6.88 (1H, ddd, J=8.2, 7.3, 1.2 Hz), 6.81 (1H, dd, J=7.8, 1.2 Hz), 3.32 (3H, s), 3.27 (3H, s); $^{13}$C (75 MHz, $CDCl_3$) δ 146.5 (q), 143.5 (q), 142.1 (q), 138.8 (q), 132.7 (t), 131.0 (t), 128.7 (q), 127.6 (t), 126.2 (t), 124.2 (t), 124.1 (t), 123.7 (t), 123.1 (t), 120.4 (t), 118.8 (t), 38.5, 38.1.

Synthesis of $N^1$-(2-aminophenyl)-$N^2$-(2-chlorophenyl)-$N^1$,$N^2$-dimethylbenzene-1,2-diamine (Compound 6). Compound 6 was synthesized from compound 5 according to the procedure given above for compound 3. $^1$H NMR (300 MHz, $CDCl_3$) δ 7.3 (1H, dd, J=8.0, 1.9), 7.15 (1H, 8.5, 7.3, 1.7 Hz), 7.06-6.88 (7H, m), 6.83-6.73 (2H, m), 6.60 (1H, dd, J=7.3, 1.5 Hz).

Synthesis of $N^1$-(2-(benzylamino)phenyl)-$N^2$-(2-chlorophenyl)-$N^1$,$N^2$-dimethylbenzene-1,2-diamine (Compound 7). To a solution of aniline 6 (0.045 g, 0.13 mmol) in 1 mL THF in a 24 mL screwcap vial containing a magnetic stirbar was added benzaldehyde (20 μL, 0.16 mmol). The mixture was stirred at room temperature for 5 min. Acetic acid (7 μL, 0.13 mmol) then was added, followed by sodium triacetoxyborohydride (0.033 g, 0.16 mmol). The vial was sealed with a rubber septum and brought to reflux under an atmosphere of nitrogen. The mixture was allowed to reflux until TLC indicated consumption of the starting material. The reaction then was quenched with the addition of saturated sodium bicarbonate solution and was extracted three times with diethyl ether. The organic layers were combined and dried over sodium sulfate, and the solvent was removed under reduced pressure. The product was isolated using column chromatography on silica gel eluting with 1:99 (v/v) ether:pet ether to afford the desired product as a viscous oil in 22% yield. 1H NMR (300 MHz, CDCl3) δ7.28-6.84 (15H, m), 6.70 (1H, ddd), 6.44 (1H, dd), 4.09 (2H, d), 4.27 (1H, t), 3.21 (3H, s), 3.10 (3H, s).

Example 2

Preparation of 10,15-Dihydro-5H-tribenzo[b,e,h][1,4,7]triazonine via a 2,2'-Dibromodiphenylamine Intermediate Another suitable route to 10,15-dihydro-5H-tribenzo[b,e,h][1,4,7]triazonine (formula (V)) via the 2,2'-dibromodiphenylamine intermediate 9 is outlined in Scheme 2. Compound 9 was obtained via a Buchwald-Hartwig reaction of 2-bromoaniline with 2-iodobromobenzene in the presence of catalytic $Pd_2(OAc)_2$, DPEphos, and sodium t-butoxide in toluene. Coupling of 2,2'-dibromodiphenylamine 9 with an N,N-disubstituted ortho-phenylenediamine, such as N,N-dibenzyl ortho-phenylenediamine, in the presence of catalytic $Pd_2(OAc)_2$, DPEphos, and sodium t-butoxide in toluene affords compound 10. Dealkylation of compound 10 using HCl, HBr, Krapcho conditions, chloroformate methods, Lewis acids, oxidative methods, photochemical methods, or lithium aluminum hydride provides formula (V).

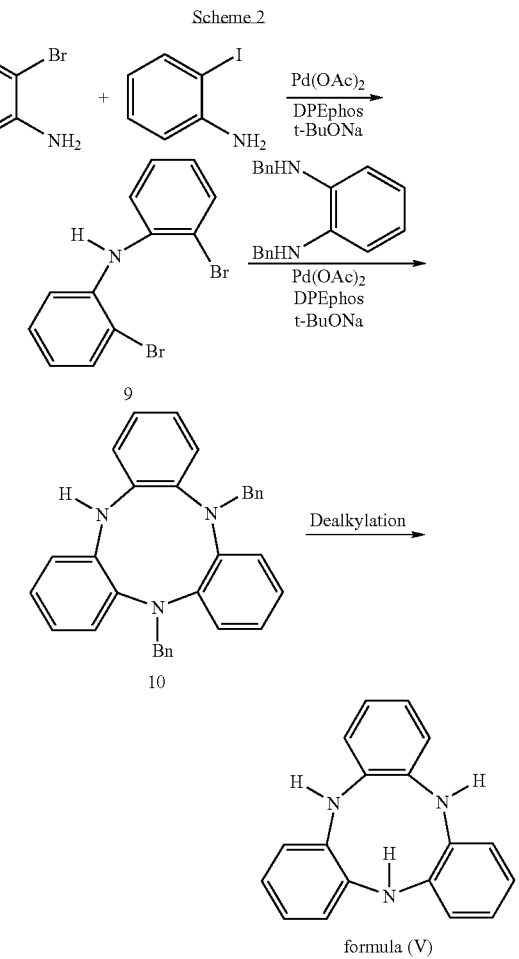

Example 3

Preparation of 10,15-Dihydro-5H-tribenzo[b,e,h][1,4,7]triazonine via a 2,2'-Diaminodiphenylamine Intermediate An additional suitable route to 10,15-dihydro-5H-tribenzo[b,e,h][1,4,7]triazonine (formula (V)) via the 2,2'-diaminodiphenylamine intermediate 12 is outlined in Scheme 3. Compound 11 was obtained via a nucleophilic aromatic substitution reaction of 2-nitrobromobenzene with 2-nitroaniline in the presence of potassium carbonate at 160° C. for 16 hours in DMSO. The dinitrodiphenylamine compound 11 was reduced using in situ-prepared diimide generated from hydrazine in refluxing ethanol in the presence of palladium on carbon. Reductive amination of the resulting 2,2'-diaminodiphenylamine 12 with an aldehyde, such as benzaldehyde, in the presence of a borohydride such as triacetoxyborohydride furnishes compound 13. Buchwald-Hartwig cyclization of compound 13 using, for example, 1,2-diiodobenzene, $Pd_2(dba)_3$, BINAP, and cesium carbonate affords the cyclic N,N-disubstituted compound 14. Dealkylation of compound 14 using HCl, HBr, Krapcho conditions, chloroformate methods, Lewis acids, oxidative methods, photochemical methods, or lithium aluminum hydride provides formula (V).

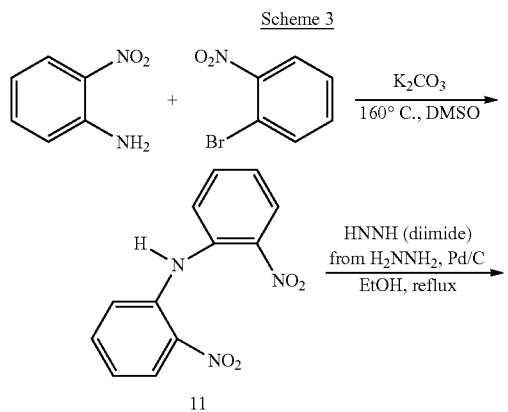

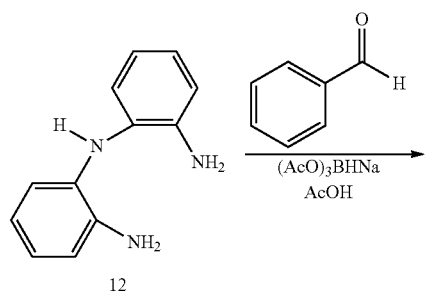

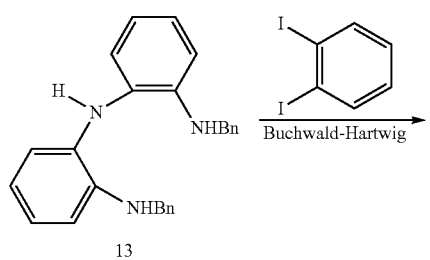

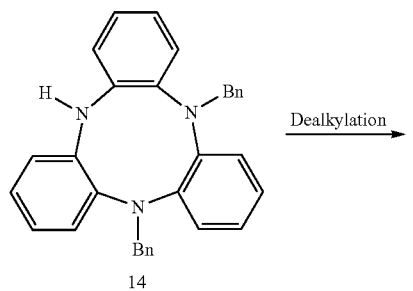

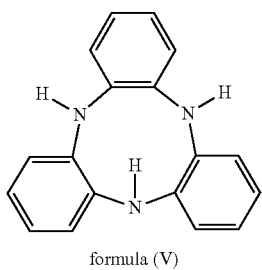

formula (V)

What is claimed is:

1. A compound of formula (I) or a salt or metal complex thereof:

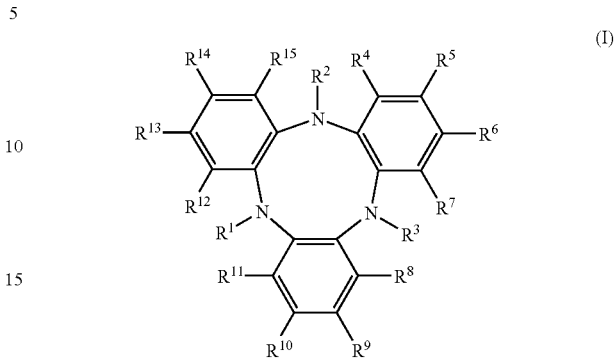

wherein:
R$^1$, R$^2$, and R$^3$ are each independently selected from the group consisting of: H, optionally substituted linear or branched C$_1$ to C$_{20}$ alkyl, optionally substituted linear or branched C$_2$ to C$_{20}$ alkenyl, optionally substituted linear or branched C$_2$ to C$_{20}$ alkynyl, optionally substituted C$_3$ to C$_{20}$ alicyclic, aryl, heteroaryl, optionally substituted C$_1$ to C$_{20}$ alkylene-aryl, optionally substituted C$_1$ to C$_{20}$ alkylene-heteroaryl, and C$_1$ to C$_{20}$ alkylene-X$^1$; or R$^1$, R$^2$, and R$^3$ taken together are CR$^z$, B, or a metal;

R$^z$ is selected from the group consisting of Li, H, optionally substituted linear or branched C$_1$ to C$_{20}$ alkyl, optionally substituted linear or branched C$_2$ to C$_{20}$ alkenyl, optionally substituted linear or branched C$_2$ to C$_{20}$ alkynyl, optionally substituted C$_3$ to C$_{20}$ alicyclic, aryl, heteroaryl, optionally substituted C$_1$ to C$_{20}$ alkylene-aryl, and optionally substituted C$_1$ to C$_{20}$ alkylene-heteroaryl;

R$^4$, R$^5$, R$^6$, R$^7$, R$^8$, R$^9$, R$^{10}$, R$^{11}$, R$^{12}$, R$^{13}$, R$^{14}$, and R$^{15}$ are each independently selected from the group consisting of: H, F, Cl, Br, I, —NO$_2$, —CN, —C(O)OH, —C(O)OR$^c$, —C(O)H, —C(O)R$^c$, —C(O)NH$_2$, —C(O)NHR$^c$, —C(O)NR$^c$R$^d$, —C(O)SR$^c$, —NH$_2$, —NHR$^c$, —NR$^c$R$^d$, —OH, —OR$^c$, —SH, —SR$^c$, optionally substituted linear or branched C$_1$ to C$_{20}$ alkyl, optionally substituted linear or branched C$_2$ to C$_{20}$ alkenyl, optionally substituted linear or branched C$_2$ to C$_{20}$ alkynyl, optionally substituted C$_3$ to C$_{20}$ alicyclic, aryl, heteroaryl, optionally substituted C$_1$ to C$_{20}$ alkylene-aryl, optionally substituted C$_1$ to C$_{20}$ alkylene-heteroaryl, and C$_1$ to C$_{20}$ alkylene-X$^2$;

X$^1$ and X$^2$ are each independently selected from the group consisting of: —C(O)OH, —C(O)OR$^a$, —C(O)H, —C(O)R$^a$, —C(O)NH$_2$, —C(O)NHR$^a$, —C(O)NR$^a$R$^b$, —C(O)SR$^a$, —NH$_2$, —NHR$^a$, —NR$^a$R$^b$, —OH, OR$^a$, —SH, and SR$^a$; and R$^a$, R$^b$, R$^c$, and R$^d$ are each independently selected from the group consisting of: optionally substituted linear or branched C$_1$ to C$_{20}$ alkyl, optionally substituted linear or branched C$_2$ to C$_{20}$ alkenyl, optionally substituted linear or branched C$_2$ to C$_{20}$ alkynyl, optionally substituted C$_3$ to C$_{20}$ alicyclic, aryl, heteroaryl, optionally substituted C$_1$ to C$_{20}$ alkylene-aryl, and optionally substituted C$_1$ to C$_{20}$ alkylene-heteroaryl.

2. The compound of claim 1 having a formula (I) or a salt or metal complex thereof wherein R$^4$, R$^5$, R$^6$, R$^7$, R$^8$, R$^9$, R$^{10}$, R$^{11}$, R$^{12}$, R$^{13}$, R$^{14}$, and R$^{15}$ are each independently selected from the group consisting of: H, F, Cl, Br, and I.

3. The compound of claim 1 having a formula (II) or a salt or metal complex thereof:

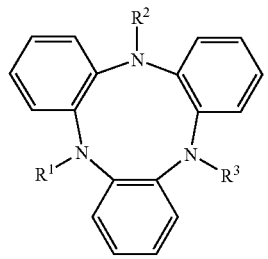

(II)

wherein:
- $R^1$, $R^2$, and $R^3$ are each independently selected from the group consisting of: H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^1$; or
- $R^1$, $R^2$, and $R^3$ taken together are $CR^z$, B, or a metal;
- $R^z$ is selected from the group consisting of Li, H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl;
- $X^1$ is selected from the group consisting of: —C(O)OH, —C(O)OR$^a$, —C(O)H, —C(O)R$^a$, —C(O)NH$_2$, —C(O)NHR$^a$, —C(O)NR$^a$R$^b$, —C(O)SR$^a$, —NH$_2$, —NHR$^a$, —NR$^a$R$^b$, —OH, —OR$^a$, —SH, and —SR$^a$; and
- $R^a$ and $R^b$ are each independently selected from the group consisting of: optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl.

4. The compound of claim 3 having a formula (II) or a salt or metal complex thereof:
wherein:
- $R^1$, $R^2$, and $R^3$ are each independently selected from the group consisting of: H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^1$;
- $X^1$ is —C(O)OH, —C(O)OR$^a$, —C(O)H, —C(O)R$^a$, —C(O)NH$_2$, —C(O)NHR$^a$, —C(O)NR$^a$R$^b$, —C(O)SR$^a$, —NH$_2$, —NHR$^a$, —NR$^a$R$^b$, —OH, —OR$^a$, —SH, or —SR$^a$; and
- $R^a$ and $R^b$ are each independently selected from the group consisting of: optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl.

5. The compound of claim 1 having a formula (III) or a salt or metal complex thereof:

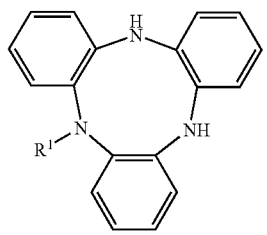

(III)

wherein:
- $R^1$ is H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, or $C_1$ to $C_{20}$ alkylene-$X^1$;
- $X^1$ is —C(O)OH, —C(O)OR$^a$, —C(O)H, —C(O)R$^a$, —C(O)NH$_2$, —C(O)NHR$^a$, —C(O)NR$^a$R$^b$, —C(O)SR$^a$, —NH$_2$, —NHR$^a$, —NR$^a$R$^b$, —OH, —OR$^a$, —SH, or —SR$^a$; and
- $R^a$ and $R^b$ are each independently selected from the group consisting of: optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, and optionally substituted $C_1$ to $C_{20}$ alkylene-heteroaryl.

6. The compound of claim 1 having a formula:

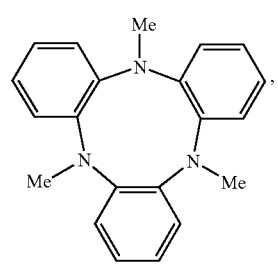

(XXI)

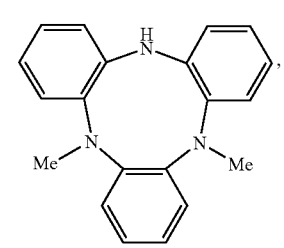

(IV)

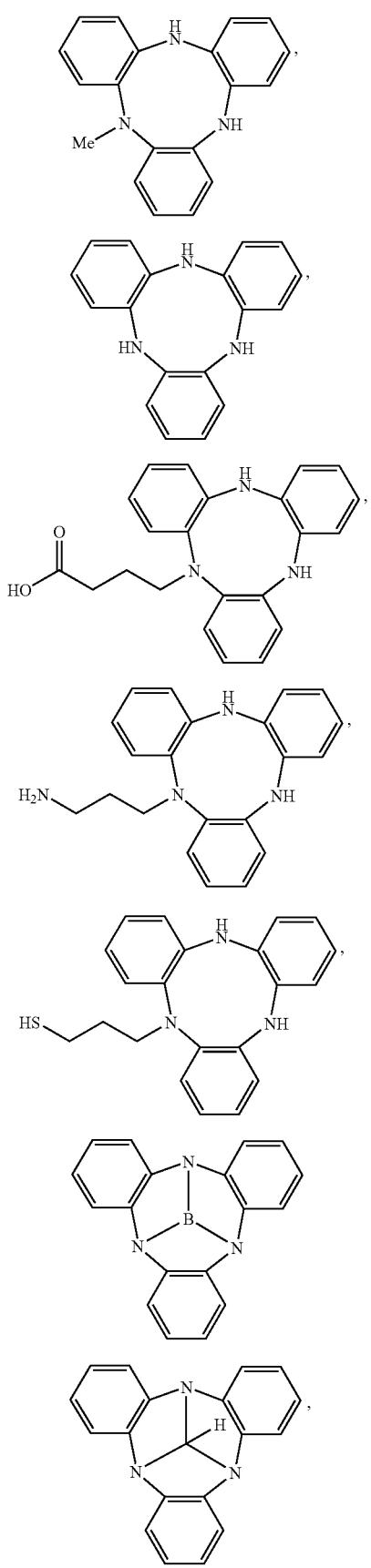

(XXII)

(V)

(VI)

(VII)

(VIII)

(IX)

(X)

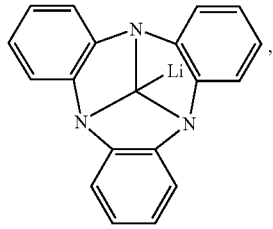

(XA)

or a salt or metal complex thereof.

7. The compound of claim 1 wherein the metal is selected from the group consisting of Li, Na, K, Zn, Cu, Co, Ni, Mo, and Gd.

8. A method of preparing 10,15-dihydro-5H-tribenzo[b,e,h][1,4,7]triazonine or a derivative thereof comprising:
(i) subjecting a compound of formula (XI) to conditions sufficient to form a compound of formula (XII):

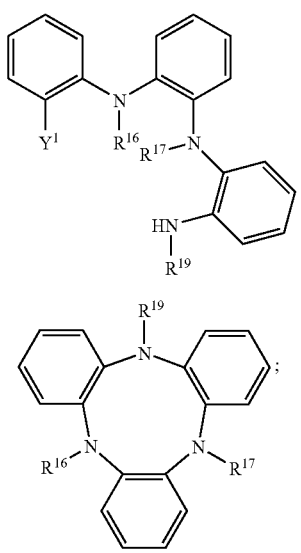

(XI)

(XII)

wherein $Y^1$ is F, Cl, Br, I, or a sulfonate leaving group;
$R^{16}$ and $R^{17}$ are each independently selected from the group consisting of: optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^3$;
$R^{19}$ is selected from the group consisting of: H, optionally substituted linear or branched $C_1$ to $C_{20}$ alkyl, optionally substituted linear or branched $C_2$ to $C_{20}$ alkenyl, optionally substituted linear or branched $C_2$ to $C_{20}$ alkynyl, optionally substituted $C_3$ to $C_{20}$ alicyclic, aryl, heteroaryl, optionally substituted $C_1$ to $C_{20}$ alkylene-aryl, optionally substituted $C_1$ to $C_{20}$ alkylene-heteroaryl, and $C_1$ to $C_{20}$ alkylene-$X^4$;
$X^3$ and $X^4$ are each independently selected from the group consisting of: —C(O)OH, —C(O)OR$^a$, —C(O)H, —C(O)R$^a$, —C(O)NH$_2$, —C(O)NHR$^a$, —C(O)NR$^a$R$^b$, —C(O)SR$^a$, —NH$_2$, —NHR$^a$, —NR$^a$R$^b$, —OH, —OR$^a$, —SH, and —SR$^a$;

R$^a$ and R$^b$ are each independently selected from the group consisting of: optionally substituted linear or branched C$_1$ to C$_{20}$ alkyl, optionally substituted linear or branched C$_2$ to C$_{20}$ alkenyl, optionally substituted linear or branched C$_2$ to C$_{20}$ alkynyl, optionally substituted C$_3$ to C$_{20}$ alicyclic, aryl, heteroaryl, optionally substituted C$_1$ to C$_{20}$ alkylene-aryl, and optionally substituted C$_1$ to C$_{20}$ alkylene-heteroaryl; and (ii) subjecting a compound of formula (XII) to conditions sufficient to form a compound of formula (V):

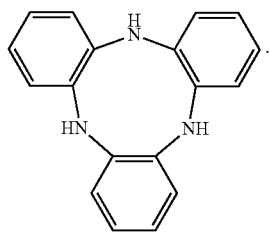
(V)

9. The method of claim 8, wherein the conditions sufficient to form a compound of formula (XII) comprise admixing the compound of formula (XI), a catalyst, and a base.

10. The method of claim 8 further comprising:

subjecting a compound of formula (XIII) to conditions sufficient to form a compound of formula (XI):

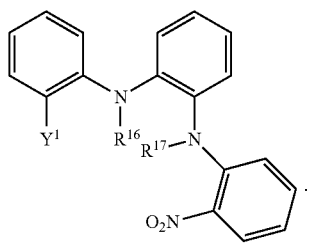
(XIII)

11. The method of claim 10 further comprising:

subjecting a compound of formula (XIV) in the presence of a compound of formula R$^{17}$—Z to conditions sufficient to form a compound of formula (XIII):

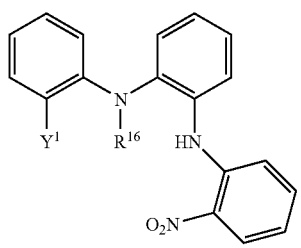
(XIV)

wherein Z is a leaving group.

12. The method of claim 11 further comprising:

subjecting a mixture comprising a compound of formula (XV) and a compound of formula (XVA) to conditions sufficient to form a compound of formula (XIV):

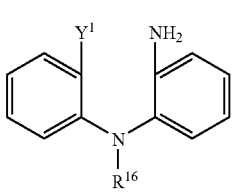
(XV)

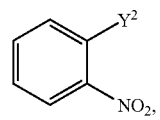
(XVA)

wherein Y$^2$ is F, Cl, Br, I, or a sulfonate leaving group, with the proviso that Y$^2$ is different from Y$^1$.

13. The method of claim 12, wherein the conditions sufficient to form a compound of formula (XIV) comprise admixing the compound of formula (XV), the compound of formula (XVA), a catalyst, and a base.

14. A method of preparing a derivative of 10,15-dihydro-5H-tribenzo[b,e,h][1,4,7]triazonine comprising:

subjecting a compound of formula (XIIA) in the presence of a compound of formula R$^{18}$—Z to conditions sufficient to form a compound of formula (XX):

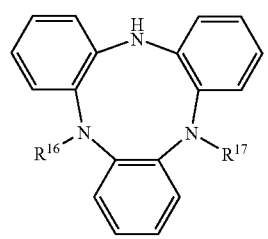
(XIIA)

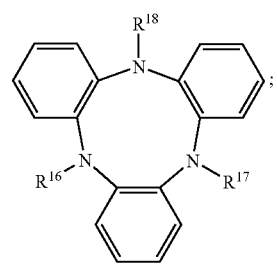
(XX)

wherein R$^{16}$, R$^{17}$, and R$^{18}$ are each independently selected from the group consisting of: optionally substituted linear or branched C$_1$ to C$_{20}$ alkyl; optionally substituted linear or branched C$_2$ to C$_{20}$ alkenyl; optionally substituted linear or branched C$_2$ to C$_{20}$ alkynyl; optionally substituted C$_3$ to C$_{20}$ alicyclic; aryl; heteroaryl; optionally substituted C$_1$ to C$_{20}$ alkylene-aryl; optionally substituted C$_1$ to C$_{20}$ alkylene-heteroaryl; and C$_1$ to C$_{20}$ alkylene-X;

X is —C(O)OH, —C(O)OR$^a$, —C(O)H, —C(O)R$^a$, —C(O)NH$_2$, —C(O)NHR$^a$, —C(O)NR$^a$R$^b$, —C(O)SR$^a$, —NH$_2$, —NHR$^a$, —NR$^a$R$^b$, —OH, —OR$^a$, —SH, or —SR$^a$;

$R^a$ and $R^b$ are each independently selected from the group consisting of: optionally substituted linear or branched $C_1$ to $C_{20}$ alkyl; optionally substituted linear or branched $C_2$ to $C_{20}$ alkenyl; optionally substituted linear or branched $C_2$ to $C_{20}$ alkynyl; optionally substituted $C_3$ to $C_{20}$ alicyclic; aryl; heteroaryl; optionally substituted $C_1$ to $C_{20}$ alkylene-aryl; and optionally substituted $C_1$ to $C_{20}$ alkylene-heteroaryl; and Z is a leaving group.

* * * * *